United States Patent [19]

Bernarducci, Ernest et al.

[11] Patent Number: 5,163,616
[45] Date of Patent: Nov. 17, 1992

[54] AIR FRESHENER DEVICE WITH VISUAL SIGNAL MEANS

[75] Inventors: Bernarducci, Ernest, Rutherford; Kenneth Ward, Dumont; Edward Morris, Paramus, all of N.J.

[73] Assignee: Block Drug Company, Inc., Jersey City, N.J.

[21] Appl. No.: 640,947

[22] Filed: Jan. 14, 1991

[51] Int. Cl.⁵ ............................... A61L 9/04
[52] U.S. Cl. ............................. 239/35; 239/60
[58] Field of Search ............... 239/34, 35, 44, 49, 239/51.5, 53–60

[56] References Cited

U.S. PATENT DOCUMENTS

| | | | |
|---|---|---|---|
| 2,103,609 | 12/1937 | Bradburn | 239/54 |
| 2,555,047 | 5/1951 | Logue | 239/57 |
| 2,642,310 | 6/1953 | Meek et al. | 239/35 |
| 3,797,742 | 3/1974 | Clark et al. | 239/60 |
| 4,712,737 | 12/1987 | Hecking | 239/58 |
| 4,824,707 | 4/1989 | Spector | 239/35 |

FOREIGN PATENT DOCUMENTS 2253536 7/1975 France ............................ 239/34

Primary Examiner—Andres Kashnikow
Assistant Examiner—Karen B. Merritt
Attorney, Agent, or Firm—Ostrolenk, Faber, Gerb & Soffen

[57] ABSTRACT

An air freshener device which indicates when air freshening fragrance formulation contained therein is consumed. The device has a plurality of chambers which contain the same or different fragrance formulations. The inner walls of the chambers are contrastingly colored with respect to the fragrance formulation so that, when the fragrance formulation is consumed, the colored walls are exposed indicating to the user that the formulation within that chamber has been depleted. The multi-chamber feature of the device provides the possibility of multiple fragrance choices and, at the same time, allows for the release of fragrance for an extended period of time.

3 Claims, 3 Drawing Sheets

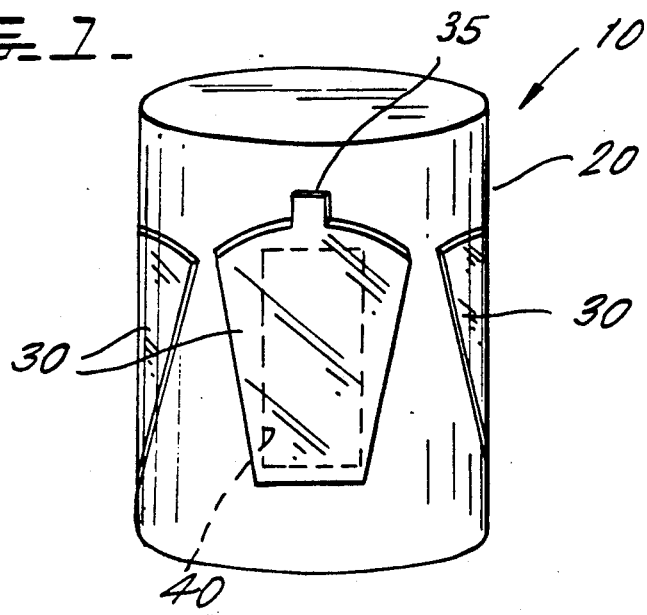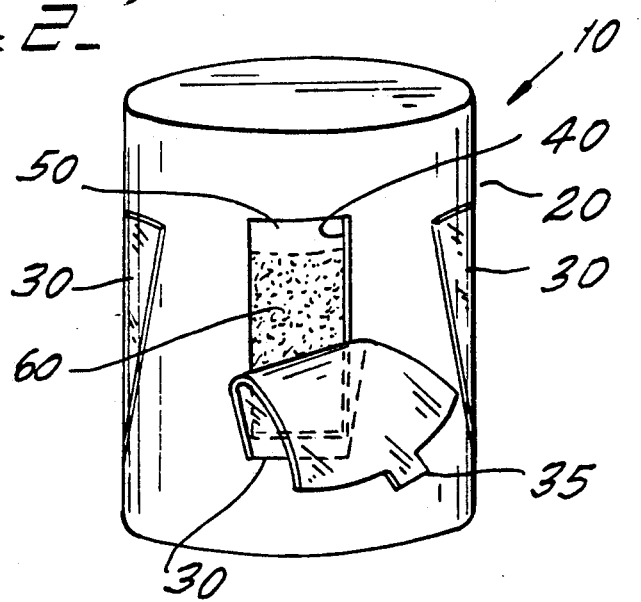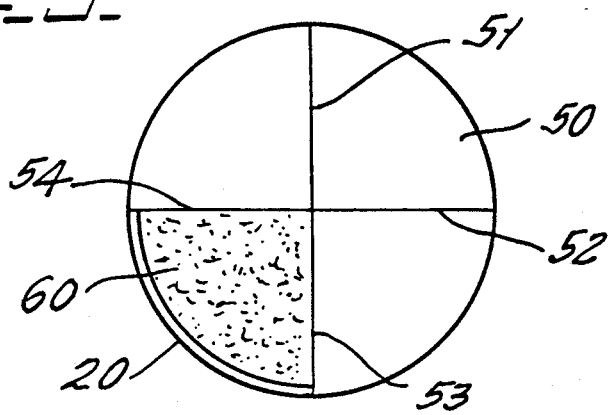

AIR FRESHENER DEVICE WITH VISUAL SIGNAL MEANS

BACKGROUND OF THE INVENTION

1. Field of the Invention:

The present invention relates to an air freshener device and, more particularly, a multichamber air freshener device which (1) releases fragrance for an extended period of time; (2) provides the possibility of multiple fragrance choices for each individual device; and (3) includes a visual signal to replace the device.

2. Description of the Related Art:

Typical air fresheners or room deodorizers currently marketed release fragrance into the environment for 30 days or 40 days before needing to be replaced. They seldom offer a visual signal to the user to replace the depleted unit and never offer a choice of fragrances in one individual unit U.S. Pat. No. 2,555,047 to Logue discloses a sachet holder which can provide different scents. The sachet holder includes compartments for differently fragranced sachets and means for selectively and individually exposing the different sachets for scent radiation.

More modern scent radiating devices are typified by the air freshener devices taught by U.S. Pat. Nos. 4,712,737 to Hecking, 2,878,060 to Russo, and 3,104,816 to Jaffe. Hecking teaches a container for air freshening similar to a standard milk carton and including openings sealed with removable tape. Russo teaches a conventional vapor diffusing or air freshener device which includes a base having upwardly oriented fingers which grip a movable closure which is lifted to expose a slug of fragrant gel. Jaffe teaches a dispenser or air freshener device similar to that taught by Russo, but having an end point indicating means A spring is provided underneath the base, the spring being compressed by the weight of the fragrant gel slug until the slug is consumed At that time, the slug no longer compresses the spring which then tilts the device to indicate it needs recharging.

These patents do not disclose or suggest a single air freshener device having a construction which provides the combined features of: (1) increased usable life; (2) a visual signal of fragrance depletion; and (3) multiple fragrance choices within the single device Also, the known end point indicating means is unsatisfactory. It utilizes mechanical means which are subject to failure.

SUMMARY OF THE INVENTION

Accordingly, an object of the invention is to provide a solid air freshener or room deodorizer device that: (1) delivers fragrance to an environment for an extended period of time, preferably at least four full months; (2) provides to the consumer a variety of fragrance types from which to choose in a single solid air freshener or room deodorizer unit; and (3) provides to the consumer a visual signal to replace the unit upon depletion of all fragrance types provided in each unit.

Another objective of the invention is to provide an air freshener device having an improved visual signal to replace the device.

These and other objectives, are achieved by providing an air freshener device including a canister for holding one or more air freshening fragrance formulations. The canister has a plurality of chambers which contain the same or differently scented fragrance formulations. A plurality of apertures are provided in the canister, each chamber having one or more apertures associated therewith, the apertures being covered by removable seals prior to use. Each chamber includes means to visually signal that the fragrance formulation therein is depleted Preferably, the means comprises the inner walls of the chambers, which are contrastingly colored with respect to the fragrance formulation such that depletion of the fragrance formulation exposes the colored chamber walls.

A method of radiating a fragrance from an air freshener device is also provided The method includes containing one or more fragrance formulations in the device described above, removing a seal from the device to allow fragrance to radiate from exposed fragrance formulation, visually inspecting the visual signaling means to determine if the fragrance formulation in the opened chamber is depleted, and if so, removing another seal This procedure is repeated until all the chambers have been opened and all the fragrance formulation has been depleted.

BRIEF DESCRIPTION OF THE DRAWINGS

Other features and advantages of the present invention will become apparent when the following description is read in conjunction with the accompanying drawings, in which:

FIG. 1 is a perspective looking at the side and top of the air freshener device of the invention prior to use;

FIG. 2 is a side view of the device during use, a seal having been partially removed to expose a fragrance formulation;

FIG. 3 is a top view of the device, a top cover having been removed to expose the interior of the device and show the interior fragrance formulation-containing chambers, and fragrance formulation contained in one of the chambers;

DETAILED DESCRIPTION OF THE PREFERRED EMBODIMENTS

Figure 4:
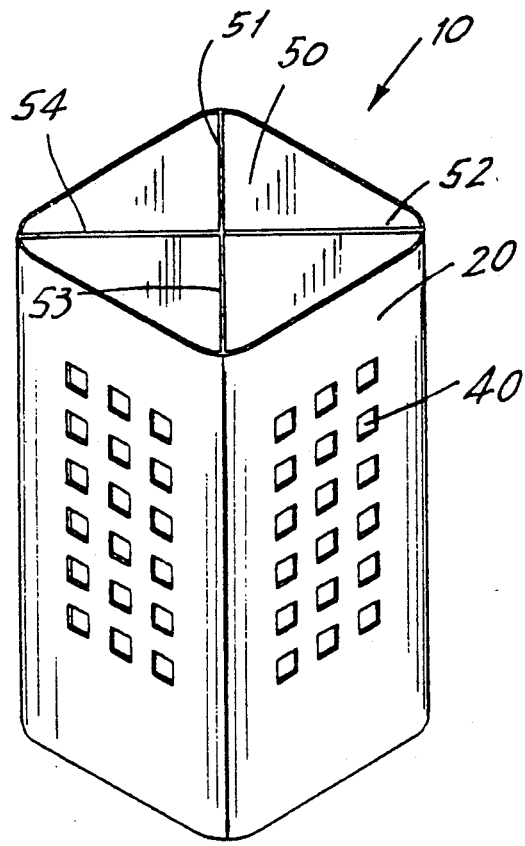
FIG. 4 is a perspective looking toward the top of an air freshener device of the invention, a top cover having been removed to expose the interior of the device and show the interior fragrance formulation-containing chambers, and seals having been removed to expose numerous scent radiating apertures.

Referring now to the drawings wherein like numbers indicate like elements, there is shown in FIG. 1 an air freshener device in accordance with the principles of the invention and designated generally as 10. Air freshener device 10 includes a canister 20 having numerous peel-away sea&s 30 which each releasably cover corresponding apertures 40 leading into chambers 50, defined by chamber walls 51, 52, 53 and 54, which contain fragrance formulation 60.

Figure 6:
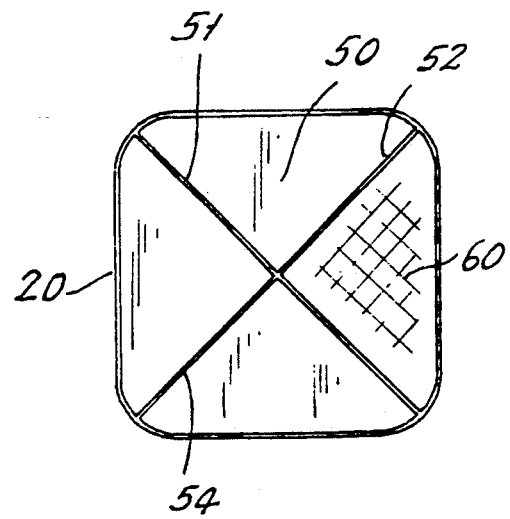
FIG. 6 is a top view of the device shown in FIGS. 4 and 5, a top cover having been removed to expose the interior of the device and show the interior fragrance formulation-containing chambers, and fragrance formulation contained within one chamber.
Figure 5:
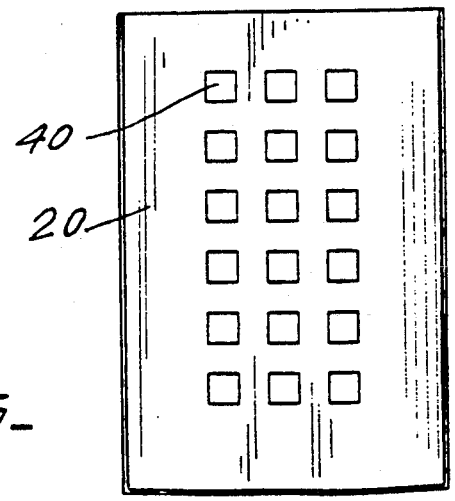
FIG. 5 is a side view of the device shown in FIG. 4.
Figure 8:
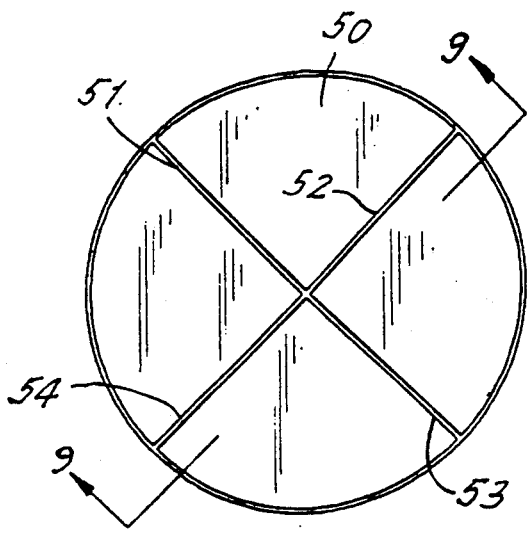
FIG. 8 is a top view of the device shown in FIG. 7, a top cover having been removed to expose the interior of the device and show the interior fragrance formulation-containing chambers.
Figure 7:
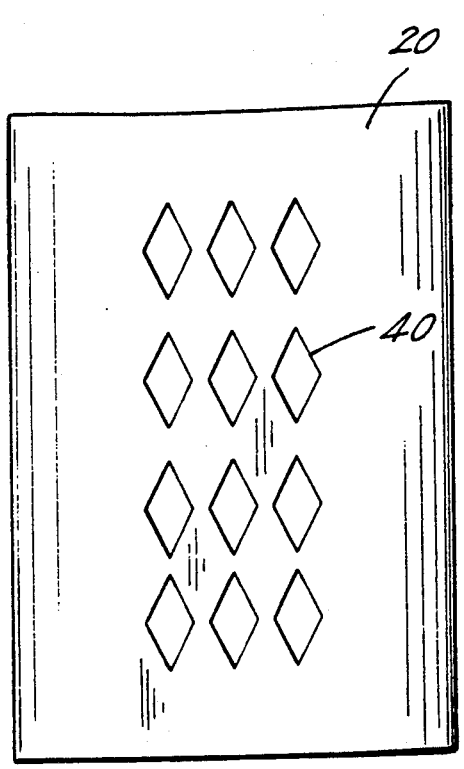
FIG. 7 is a side view of an air freshener device of the invention, a seal having been removed to expose numerous scent radiating apertures.
Figure 9:
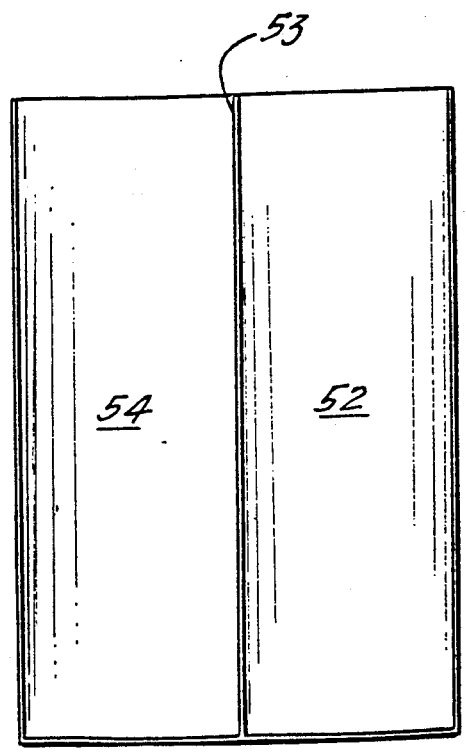
FIG. 9 is a cross-section of the device shown in FIGS. 7 and 8 taken along lines 9—9 in FIG. 8.

The overall aesthetic design of the solid air freshener device or room deodorizer unit 10 will be dictated by current trends and styles. Many sizes and shapes are possible and will be apparent to one skilled in the art A cylindrical shape or configuration is shown in FIGS. 1-3 and 7-9, while a square shape or configuration is shown in FIGS. 4-6.

In this preferred example (FIGS. 1-3), each individual device 10 has as its core four separate chambers 50 Other designs may have more or less. The chambers 50 are separated from one another by four walls 51-54 These walls serve to prevent contamination or interaction between the freshener within the chambers.

Chambers 50 open to the outside environment through respective apertures 40 located in the side of device 10. Although FIG. 2 shows a rectangular opening, apertures 40 may be of any desired shape, and may comprise a pattern of apertures, such as a pattern of square-shaped apertures (FIGS. 4-6) or diamond-shaped apertures (FIGS. 7-9) Apertures 40 may be covered by a grid (not shown) for controlled fragrance diffusion, child safety and other advantages which will be apparent to one skilled in the art. Each chamber 50 is filled with air freshener or room deodorizer formulation 60 such as a gel, provided in sufficient quantity to last approximately 30 days. Since the chambers 50 are isolated from one another by walls 51-54, each chamber may contain a freshener with a different scent. Each aperture 40 is individually sealed by a peel-away seal 30, which includes a conventional releasable adhesive on a side of the seal which contacts canister 20, so as to open one aperture 40 at a time. If so desired this seal 30 can be designed to be resealable. It will be understood that other means, such as a snap-on arrangement, can be used to fasten seals 30 to device 10. These can also be resealable. Seal 30 is removed to expose a chamber 50 to freshen a room with the particular fragrance uncovered. Although FIG. 2 shows a seal 30 having the shape of a truncated cone with a rounded top, seals 30 may be of any desired shape A tab 35 is provided at the top of seal 30 to assist the user in gripping and removing seal 30.

The fragrance formulation 60 in each chamber preferably is provided in a color which contrasts with the color of the surfaces of inner walls 51-54 of chambers 50. Thus, as formulation 60 dissipates throughout the course of a mouth, it shrinks to eventually expose the contrastingly colored inner walls 51-54 of chambers 50, thereby signaling to the user that it is time to open the next chamber 50. By way of example, formulation 60 may be green, while inner walls 51-54 may be white It will be understood that for each chamber 50, only one inner wall need be colored, but both may be colored. When an inner wall 51, 52, 53 or 54 becomes visible, the next peel-away seal 30 would be removed exposing the next fragrance formulation 60. The user can continue to use device 10 until all four chambers 50 are opened and all formulations 60 are dissipated As stated above, the walls 51-54 which divide the interior of canister 20 are constructed to eliminate cross contamination among chambers 50. In this regard, canister 20 and inner walls 51-54 may be constructed of any suitable material that is impervious to the fragrance formulation. This allows for the use of multiple fragrance types to provide the consumer with a choice of up to four different fragrances per device If more chambers are designed into the unit, more fragrances can be used Although the present invention has been described in connection with the preferred embodiment thereof, many other variations and modifications will now become apparent to those skilled in the art without departing from the scope of the invention. It is preferred, therefore, that the present invention be limited not by the specific disclosure herein, but only by the appended claims

What is claimed is:

1. A method of radiating a fragrance from an air freshener device, comprising the steps of:
   a) containing at least one air freshening fragrance formulation in a canister having a plurality of chambers, an individual aperture means for each of said chambers to connect the latter with atmosphere, an individually removable seal means for closing each of said aperture means, and visual signaling means for each of said chambers to indicate when said air freshening fragrance formulation therein has been depleted;
   b) removing a first of said seal means from said canister to allow said fragrance to dissipate into the environment from said first chamber;
   c) sighting through said aperture means for inspecting said visual signaling means to determine if said formulation in said first chamber is depleted;
   d) removing a second of said means from said canister to allow additional fragrance to radiate from said formulation contained in a second chamber of said container;
   e) repeating steps b) through d) until all of said formulation in all of said chambers is depleted.

2. The method of claim 1, wherein said additional fragrance is different from said fragrance radiated from said device by removal of said first seal.

3. The method of claim 1, wherein said visual signaling means comprises inner walls of said chambers, said walls being contrastingly colored with respect to said air freshening fragrance formulation such that consumption of said fragrance formulation within a chamber is indicated by exposure of said colored inner walls of that chamber.

* * * * *